United States Patent [19]

Thompson et al.

[11] 4,277,601

[45] Jul. 7, 1981

[54] PREPARATION OF SODIUM CEFUROXIME

[75] Inventors: Eric Thompson; Christopher J. Baalham, both of Ulverston, England

[73] Assignee: Glaxo Group Limited, England

[21] Appl. No.: 121,531

[22] Filed: Feb. 14, 1980

[30] Foreign Application Priority Data

Feb. 15, 1979 [GB] United Kingdom ............... 05456/79

[51] Int. Cl.³ ............................................. C07D 501/34
[52] U.S. Cl. ........................................... 544/22; 544/20
[58] Field of Search .......................................... 544/22

[56] References Cited

U.S. PATENT DOCUMENTS

| | | | |
|---|---|---|---|
| 3,905,963 | 9/1975 | Webber | 544/22 |
| 3,974,153 | 8/1976 | Cook et al. | 544/22 |
| 4,128,715 | 12/1978 | Sharp | 544/22 |

*Primary Examiner*—Paul M. Coughlan, Jr.
*Attorney, Agent, or Firm*—Bacon & Thomas

[57] ABSTRACT

A process for the preparation of the sodium salt of the antibiotic (6R,7R)-3-carbamoyloxymethyl-7-[Z-2-(fur-2-yl)-2-methoxyiminoacetamido]-ceph-3-em-4-carboxylic acid (cefuroxime) which comprises subjecting a corresponding 3-N-protected carbamoyloxymethyl compound to alcoholysis in a substantially anhydrous medium using a basic catalyst comprising the sodium salt of an acid having a $pK_a$ value of not less than 3.5 whereby sodium cefuroxime or a solvate thereof can be obtained directly without isolation of the corresponding acid. Sodium cefuroxime tetrahydrofuran solvate is also provided as a new entity.

7 Claims, No Drawings

PREPARATION OF SODIUM CEFUROXIME

This invention relates to a new process for the preparation of the sodium salt of the cephalosporin antibiotic (6R,7R)-3-carbamoyloxymethyl-7-[Z-2-(fur-2-yl)-2-methoxyiminoacetamido]ceph-3-em-4-carboxylic acid, which has the approved name "cefuroxime".

Cefuroxime, as described and claimed in U.S. Pat. No. 3,974,153 of Cook et al. is a valuable broad spectrum antibiotic characterised by high activity against a wide range of gram-positive and gram-negative microorganisms, this property being enhanced by the very high stability of the compound to β-lactamases produced by a range of gram-negative microorganisms. Additionally the compound is stable in the body owing to its resistance to the action of mammalian esterases, and gives high serum levels following parenteral administration to human and animal subjects, while exhibiting low serum binding.

Cefuroxime may be administered, in human or veterinary medicine, as a non-toxic derivative, i.e. one which is physiologically acceptable in the dosage at which it is administered. Such non-toxic derivatives conveniently include those salts, e.g., alkali metal, alkaline earth metal and organic base salts which on admixture with sterile, pyrogen-free water form aqueous solutions or suspensions for injection. In said Cook et al. U.S. Pat. No. 3,974,153 the sodium salt of cefuroxime is described as being a substance well suited to administration on injection. For convenience this sodium salt will hereinafter be referred to as sodium cefuroxime.

One process described by Cook et al. for the preparation of the parent antibiotic, cefuroxime, involves the carbamoylation of an appropriate 3-hydroxymethyl compound with inter alia an isocyanate of formula RNCO (wherein R is a labile substituent) and subsequent cleavage of the N-protected carbamoyloxymethyl group at the 3-position to form the desired 3-carbamoyloxymethyl compound. The parent acid may then be treated with for example sodium 2-ethylhexanoate to form sodium cerfuroxime. Cleavage of the above-mentioned N-protected group may be effected for example by aqueous hydrolysis in the presence of methanol and sodium bicarbonate.

There are disadvantages in carrying out the above cleavage in an aqueous medium. The carbamoylation of the appropriate 3-hydroxymethyl compound is preferably effected in non-hydroxylic solvents and hence an extraction is necessary to transfer the product to an aqueous medium. Unless the extract is subjected to further treatment, this extraction will not generally provide an aqueous solution at a suitable concentration for direct isolation of the cefuroxime as the sodium salt, particularly in view of the solubility of the salt in water.

We have now discovered that the 3-N-protected carbamoyloxymethyl group can be cleaved in such a manner that sodium cefuroxime can be obtained directly without the need to isolate the parent acid. The resulting sodium cefuroxime can thus be obtained in good yield and with good purity and crystallinity. Moreover, the resulting sodium cefuroxime can be readily recrystallised under sterile conditions.

According to a preferred feature of the present invention we provide a process for the preparation of sodium cefuroxime, if desired as a solvate, which comprises subjecting a compound of formula

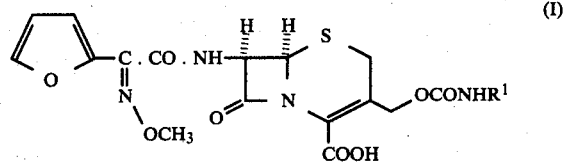

(wherein $R^1$ is a base-labile group) to alcoholysis in a substantially anhydrous solvent medium in the presence of a basic catalyst soluble in the said medium which basic catalyst comprises the sodium salt of an acid having a $pK_a$ value not less than 3.5, and subsequently recovering sodium cefuroxime or a solvate thereof. Examples of base-labile groups $R^1$ which may be readily cleaved in the above-described process include chlorinated lower (e.g. $C_{1-4}$) alkanoyl groups such as di- or tri-chloroacetyl.

The sodium salt employed as basic catalyst in the above process may be selected from the sodium salts of acids having $pK_a$ values not less than 3.5 provided that the salt has sufficient solubility in the anhydrous solvent medium to impart the desired catalytic effect. The salt is preferably a salt of a carboxylic acid, particular a $C_{2-10}$ alkanoic acid, examples of such salts including sodium acetate, sodium propionate and sodium 2-ethylhexanoate, the latter being especially preferred. The base may be added to the reaction medium as a solid or as a solution in an alcohol, for example, the alcohol which is used to effect the above-mentioned alcoholysis reaction.

The alcoholysis reaction is advantageously effected using a lower ($C_{1-4}$) alkanol such as methanol, ethanol or isopropanol, methanol being particularly preferred; a glycol, for example a lower ($C_{2-6}$) alkane glycol such as ethane-1,2-diol or propane-1,2-diol, ethane-1,2-diol being particularly preferred, or a glycol having recurring units of 2 to 4 carbon atoms such as diethylene glycol; or a mixture of a lower alkanol and a glycol, methanol and/or ethane-1,2-diol being particularly preferred as a component of such a mixture.

The anhydrous solvent medium generally comprises one or more inert organic solvents, for example, aromatic solvents such as toluene; aliphatic hydrocarbons such as hexane; chlorinated hydrocarbons such as dichloromethane; esters such as ethyl acetate and butyl acetate; ketones such as acetone and methyl ethyl ketone; ethers such as tetrahydrofuran and dioxan; and nitriles such as acetonitrile.

The solvent medium is preferably selected to provide a medium in which the sodium salt of the above compound of formula (I) is substantially soluble and from which sodium cefuroxime can be readily crystallised.

A preferred solvent medium for the above alcoholysis reaction is tetrahydrofuran or a mixture thereof with dichloromethane or hexane since such solvent systems provide sodium cefuroxime in particularly good crystalline form, for example, with regard to colour and ease of characterisation. A further advantage in using solvent systems comprising tetrahydrofuran is that the resulting sodim cefuroxime is generally formed as the tetrahydrofuran solvate in a high degree of purity. A substantial proportion of the tetrahydrofuran in such a solvate may then be displaced during any filtration and/or drying procedures of the salt by, for example, washing the filtered solvate with ethanol or drying the solvate in a stream of moist air.

The alcoholysis reaction is preferably effected at an initial pH in the range 6.0 to 8.0, particularly about 7.0, although during the reaction the pH may rise to about 10. The reaction is conveniently carried out at a temperature in the range of 5° to 60° C., preferably at 15° to 30° C., a temperature of about 25° C. being particularly preferred.

The above-mentioned substantially anhydrous solvent medium preferably contains less than 1%, particularly less than 0.2%, of water.

After completion of the alcoholysis reaction, the precipitated sodium cefuroxime can be separated from the solvent medium for example by filtration and, if desired, washed with an anhydrous solvent of the type described above.

The above-identified starting material of formula (I) may be prepared for example by reaction of a corresponding 3-hydroxymethyl compound with an appropriate isocyanate of formula $R^1NCO$ (wherein $R^1$ is as defined above), e.g. as described in U.S. Pat. No. 3,974,153 of Cook et al.

The following Examples serve to illustrate the invention. All temperatures are in °C. Tetrahydrofuran is represented as THF and gas-liquid chromatography is represented as G.L.C.

Hyflo Supercel is a siliceous filter aid.

EXAMPLE 1

Sodium cefuroxime THF solvate

To a flask, protected from moisture by a silica gel tube, was added THF (60 ml), dichloromethane (25 ml) and trichloroacetyl isocyanate (6.2 ml). The solution was cooled to −10°. With efficient stirring (6R,7R)-[Z-2-(fur-2-yl)-2-methoxyiminoacetamido]-3-hydroxymethylceph-3-em-4-carboxylic acid (10.0 g) was added in one charge followed by THF (20 ml). The temperature of the slurry rose rapidly and the cooling was manipulated to give a final temperature of 5°. A slightly opaque solution had been produced after about 30 seconds. This was stirred at 5° for 10 minutes. Cooling was then discontinued and methanol (25 ml) added in one charge. The solution temperature rose almost instantaneously to 10°. After a further 5 minutes stirring the solution was filtered. Once dry the filter bed was washed with THF (10 ml) and sucked dry.

The solution was warmed to 22° and sodium 2-ethylhexanoate (17.5 g) added in one charge. All the solid had dispersed after 5 minutes stirring leaving a slightly cloudy solution. The temperature rose to 25°. The slurry was filtered after crystallisation for 2 hours without cooling. The filter cake was washed by displacement with 1:1 THF:dichloromethane (2×50 ml) and dried. The product was dried overnight at 35° in vacuo to yield *sodium cefuroxime THF solvate* (12.41 g). $[\alpha]^{20}_D +54.6°$; $E_1^{1\%}{}_{cm}$ 343. The isolated product was shown by G.L.C. to contain 12.4% w/w of THF.

EXAMPLE 2

Sodium cefuroxime THF solvate

To a flask protected from moisture by a silica gel tube was added THF (70 ml), dichloromethane (25 ml) and trichloroacetyl isocyanate (6.2 ml). The solution was cooled to −10°. With efficient stirring (6R,7R)-7-[Z-2(fur-2-yl)-2-methoxyiminoacetamido]-3-hydroxymethylceph-3-em-4-carboxylic acid (10 g) was added in one charge followed by THF (20 ml). The temperature of the mixture was allowed to rise to 5°. The slightly opaque solution was stirred at 5° for 10 minutes. Cooling was discontinued and methanol (2.5 ml) added. After a further minute a previously prepared solution of sodium 2-ethylhexanoate (12.5 g) in methanol (20 ml) was added in one charge. With stirring, the temperature of the solution was raised to 25° over 2-3 minutes. The stirrer was then stopped and the batch left for 1 hour at 25°. Crystallisation commenced about 10 minutes after the addition of the base. After 1 hour the thick slurry was stirred for 1 minute before leaving it a further hour unstirred at 25°.

The batch was filtered and the filter cake washed with 1:1 THF:dichloromethane (2×50 ml). The wet cake was dried at 35° in vacuo to produce *sodium cefuroxime THF solvate* (12.25 g). $[\alpha]^{20}_D \times 53.8°$; $E_1^{1\%}{}_{cm}$ 343. The isolated product was shown by G.L.C. to contain 10.7% w/w of THF.

EXAMPLE 3

Sodium cefuroxime

A mixture of THF (130 ml), dichloromethane (45 ml), and trichloroacetyl isocyanate (9.3 ml) was protected from moisture and cooled to −10°. To the stirred mixture was added (6R,7R)-7-[Z-2-(fur-2-yl)-2-methoxyiminoacetamido]-3-hydroxymethylceph-3-em-4-carboxylic acid (20 g) in one charge followed by THF (40 ml). The mixture was stirred for 10 minutes at 0° to +5° and then warmed to 22°, There was then added, in one charge, a solution of sodium 2-ethylhexanoate (20 g) in methanol (40 ml) and, after stirring for 1 minute, the mixture was left undisturbed at 25° for 2 hours to crystallise. The crystalline material was collected by filtration, washed with ethanol (2×100 ml), and dried in vacuo at 35° to give sodium cefuroxime (24.1 g). The isolated product was shown by G.L.C. to contain 5.3% w/w of ethanol, 0.6% w/w of THF, and 0.04% w/w of methanol.

EXAMPLE 4

Sodium cefuroxime

A mixture of THF (60 ml), dichloromethane (25 ml), and trichloroacetyl isocyanate (6.2 ml) was protected from moisture and cooled to −10°. To the stirred mixture was added (6R,7R)-7-[Z-2-(fur-2-yl)-2-methyoxyiminoacetamido]-3-hydroxymethylceph-3-em-4-carboxylic acid (10 g) in one charge followed by THF (20 ml). The mixture was stirred for 10 minutes at 0° to +5° to give a clear solution. Methanol (6.6 ml) was added, followed by portionwise addition of anhydrous sodium acetate (0.3 g) to raise the pH to 3.5. Charcoal (1 g) and filter aid (0.5 g Hyflo Supercel) were added and the mixture stirred at 10° for 20 minutes. Further anhydrous sodium acetate (5 g) was then added and the mixture stirred at 10° to 15° for 5 minutes by which time the pH had risen to 7.2. The charcoal, undissolved sodium acetate, and filter aid were removed by filtration and the filter bed washed with methanol (23 ml) containing dichloromethane (10 ml). The filtrate and washes were combined, warmed to 25°, and left undisturbed at that temperature. Crystallisation commenced after 12 minutes. After 1 hour the mixture was stirred briefly and then left undisturbed for a further 1½ hours. The crystalline material was collected by filtration, washed with THF (2×50 ml) and dried in vacuo at 35° to give sodium cefuroxime in a yield of 78.5% theory corrected for THF and sodium acetate.

EXAMPLE 5

Sodium cefuroxime THF solvate

A mixture of THF (60 ml), dichloromethane (25 ml), and trichloroacetyl isocyanate (6.2 ml) was protected from moisture and cooled to −10°. To the stirred mixture was added (6R,7R)-7-[Z-2-(fur-2-yl)-2-methoxyiminoacetamido]-3-hydroxymethylceph-3-em-4-carboxylic acid (10 g) in one charge followed by THF (20 ml). The temperature was controlled in the range 0° to +5° and the mixture stirred for 10 minutes. Ethane-1,2-diol (15 ml) was added followed by a solution of sodium 2-ethylhexanoate (10 g) in THF (20 ml) to raise the pH to 7.3. The mixture was warmed to 25° and left undisturbed for 1 hour. The mixture was then stirred briefly and left undisturbed for a further hour. The crystalline material which had separated from the mixture was collected by filtration, washed with THF (2×50 ml), and dried in vacuo at 35° to yield sodium cefuroxime (10.76 g) THF solvate. The isolated product was shown by G.L.C. to contain 8.8% w/w of THF and 0.56% w/w of ethane-1,2-diol.

EXAMPLE 6

Sodium cefuroxime

The reaction and crystallisation were performed as in Example 5. The crystalline material was collected by filtration, washed with ethanol (2×50 ml), and dried in vacuo at ambient temperature to yield sodium cefuroxime (10 g). The isolated product was shown by G.L.C. to contain 5.6% w/w of ethanol, less than 0.07% of THF, and 0,47% w/w of ethane-1,2-diol.

EXAMPLE 7

Sodium cefuroxime (6R,7R)-[Z-2-(Fur-2-yl)-2-methoxyiminoacetamido]-3-hydroxymethylceph-3-em-4-carboxylic acid (1.0 g) was stirred with acetone (20 ml) and the mixture cooled to 0°. To this mixture was added trichloroacetyl isocyanate (0.63 ml) and the temperature maintained in the range 0° to 5° with efficient stirring. After 20 minutes there was added ethanol (1 ml) followed by a solution of sodium 2-ethylhexanoate (1.2 g) in acetone (4 ml) to adjust the mixture to pH 6.5. The mixture was stirred for 2¼ hours without cooling and then filtered. The solid so obtained was washed with acetone and dried in vacuo at 35° to give sodium cefuroxime (0.9 g)

EXAMPLE 8

Sodium cefuroxime

To a mixture of 1,2-dichloroethane (140 ml) and acetone (10 ml) was added trichloroacetyl isocyanate (6.25 ml) followed by (6R,7R)-[Z-2-(fur-2-yl)-2-methoxyiminoacetamido]-3-hydroxymethyl-ceph-3em-4-carboxylic acid (10.0 g) with stirring and cooling to keep the temperature in the range 0° to 5°. The mixture was stirred for 15 minutes and acetone (10 ml ) was added. After stirring for a further 30 minutes there was added methanol (10 ml) followed by solid sodium 2-ethylhexanoate (6.2 g) to bring the mixture to pH 7. The temperature was adjusted to 25° and the mixture stirred for 4½ hours. The crystalline solid which separated from the mixture was collected by filtration, washed with one bed volume of 1,2-dichlorethane followed by two bed volumes of acetone, and dried in vacuo at 35° to give sodium cefuroxime (10.24 g).

EXAMPLE 9

Sodium cefuroxime

To ethyl acetate (125 ml) was added trichloroacetyl isocyanate (6.25 ml) followed by (6R,7R)-[Z-2-(fur-2-yl)-2-methoxyiminoacetamido]-3-hydroxymethylceph-3-em-4-carboxylic acid (10.0 g) with stirring and cooling to keep the temperature in the range 0° to 5°. A line wash of ethyl acetate (25 ml) was added and the mixture stirred for 30 minutes. Methanol (10 ml) and charcoal (1 g) were added and the mixture stirred for 5 minutes before filtration through a bed of Hyflo Supercel. The bed was washed with ethyl acetate (2×20 ml) and the colourless filtrate and washes combined. To the bulked ethyl acetate liquors was added sodium 2-ethylhexanoate (12 g) in ethyl acetate (40 ml) until the pH was 7.1. The mixture was warmed to 25° and maintained at 25° for 4½ hours with stirring. The crystalline material which separated from the mixture was collected by filtration, washed with ethyl acetate followed by acetone, and dried in vacuo at 35° to give sodium cefuroxime (11.49 g).

EXAMPLE 10

Sodium cefuroxime

To 1,2-dimethoxyethane (125 ml) was added trichloroacetyl isocyanate (6.25 ml) followed by (6R,7R)-[Z-2-(fur-2-yl)-2-methoxyiminoacetamido]-3-hydroxymethylceph-3-em-4-carboxylic acid (10.0 g) with stirring and cooling to keep the temperature in the range 0° to 5°. A line wash of 1,2-dimethoxyethane (25 ml) was added and the mixture stirred for 20 minutes. Trichloroacetyl isocyanate (3.1 ml ) was added and the mixture stirred for a further 40 minutes. Methanol (10 ml) was added followed by solid sodium 2-ethylhexanoate (12 g) to bring the mixture to pH 6.9. The mixture was warmed to 25° and stirred at 25° for 3½ hours. The crystalline material which had separated from the mixture was collected by filtration, washed with one bed volume of 1,2-dimethoxyethane followed by two bed volumes of acetone, and dried in vacuo at 35° to give sodium cefuroxime (10.16 g).

We claim:

1. In a process for the preparation of sodium cefuroxime or a solvate thereof, the improvement which comprises subjecting a compound of formula

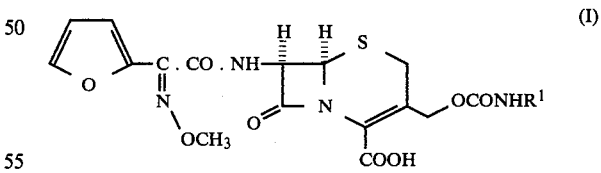

(I)

wherein $R^1$ is a base-labile group, to alcoholysis with a $C_{1-4}$ alkanol, a $C_{2-6}$ alkane glycol or a glycol having recurring units of 2 to 4 carbon atoms in a substantially anhydrous organic solvent medium in the presence of a basic catalyst soluble in the said medium, which basic catalyst comprises the sodium salt of $C_{2-10}$ alkanoic acid having a $pK_a$ value not less than 3.5.

2. A process according to claim 1 wherein $R^1$ in the compound of formula I is a chlorinated lower alkanoyl group.

3. A process according to claim 2 wherein $R^1$ in the compound of formula I is a trichloroacetyl group.

4. A process according to claim 1 wherein the basic catalyst is sodium 2-ethylhexanoate.

5. A process according to claim 1 wherein the alcoholysis is effected using at least one compound selected from the group consisting of methanol and ethane-1,2-diol.

6. A process according to claim 1 wherein the organic solvent medium is tetrahydrofuran or a mixture thereof with dichloromethane or hexane.

7. Sodium cefuroxime tetrahydrofuran solvate.

* * * * *